United States Patent [19]

Brownell

[11] Patent Number: 4,816,020

[45] Date of Patent: Mar. 28, 1989

[54] RETAINER DEVICE FOR ATTACHING MEMBERS TO FLEXIBLE TUBES AND THE LIKE TO FLEXIBLE TUBES AND THE LIKE

[75] Inventor: Richard G. Brownell, Greenwich, N.Y.

[73] Assignee: Sherwood Medical Company, St. Louis, Mo.

[21] Appl. No.: 101,801

[22] Filed: Sep. 28, 1987

[51] Int. Cl.[4] ............................................. A61M 25/00
[52] U.S. Cl. ..................................... 604/97; 604/283; 128/344
[58] Field of Search ................... 604/280, 283, 97, 98, 604/99, 247, 256; 285/282, 361; 128/344

[56] References Cited

U.S. PATENT DOCUMENTS

| | | |
|---|---|---|
| 3,087,492 | 4/1963 | Garth . |
| 3,131,694 | 5/1964 | Garth . |
| 3,356,093 | 12/1967 | Monahon . |
| 3,409,015 | 11/1968 | Swanson ................. 604/99 |
| 3,495,594 | 2/1970 | Swanson . |
| 4,232,677 | 11/1980 | Leibensohn . |
| 4,405,308 | 9/1983 | Jessup ..................... 604/200 |
| 4,430,081 | 2/1984 | Timmermans ........... 604/256 |
| 4,484,916 | 11/1984 | McPhee ................... 604/256 |
| 4,592,092 | 5/1986 | McPhee ................... 383/80 |
| 4,673,393 | 6/1987 | Suzuki et al. ........... 604/256 |

Primary Examiner—Stephen C. Pellegrino
Attorney, Agent, or Firm—Stanley N. Garber; Andrew J. Beck; William R. O'Meara

[57] ABSTRACT

A valve retainer for securely attaching a valve to a flexible tube of a medical device comprising a tubular body having tabs extending from one end of the retainer that are deflectable inwardly of the retainer to positions extending adjacent the inner surface of the retainer and the outer portion of the tube so that the tabs prevent withdrawal of the valve from the flexible tube.

20 Claims, 2 Drawing Sheets

RETAINER DEVICE FOR ATTACHING MEMBERS TO FLEXIBLE TUBES AND THE LIKE TO FLEXIBLE TUBES AND THE LIKE

This invention relates to valved medical devices and more particularly to a valve retainer for attaching a valve to a tube of a medical device.

Catheters or tubes of medical devices, such as used to drain internal organs, for example, Foley catheters for the catheterization of the bladder, generally have an inflatable cuff or balloon near the distal end of the catheter. When the catheter is inserted into the patient, the distal end and the uninflated balloon enters the bladder. Thereafter, the balloon is inflated to prevent the catheter from inadvertently moving out of the bladder. The catheter may remain in the patient over a considerable length of time. Catheters with balloons, such as Foley catheters, usually have an auxiliary or inflation lumen, for example, a lumen formed in the sidewall of the catheter tube which connects with the balloon. Usually, an inflation tube is connected to the auxiliary lumen near the proximal end of the catheter and a normally closed valve attached at the proximal end of the inflation tube.

The valve typically has a socket or bore to receive the distal end or tip of a syringe barrel which, when fully inserted into the valve, opens it and allows fluid, such as air, water, or other fluid, to pass through the valve from the syringe and to the inflation tube, lumen and balloon. When the balloon is inflated to the desired extent, the syringe is removed from the valve whereupon the valve automatically returns to its normally closed condition to thereby maintain the balloon inflated within the bladder of the patient. The syringe tip can be part way inserted into the valve to allow some fluid to escape from the balloon where it is desired to adjust the balloon pressure.

There have been certain problems associated with such valved catheters. For example, when the tip of the syringe barrel is fully inserted into the valve to open it, the tip must be seated in sealing frictional engagement with the socket of the valve so that there is no fluid leak between the valve and the tip when the syringe is forcing fluid into the inflation lumen and balloon. In many cases, the syringe tip and valve are provided with complementary luer tapered surfaces forming a fluid tight luer lock connection during inflation of the balloon. Because of the sealing frictional engagement between the syringe tip and valve during inflation of the balloon, there may be forces tending to pull the valve from the inflation tube, unless care is taken in releasing the syringe tip from the valve prior to longitudinally removing the syringe. The amount of force required to remove the syringe often depends upon the technique and force employed by the individual when inserting the syringe tip. Where the valve was loosened upon removal of the syringe tip, fluid leaks from the balloon causing deflation. If the valve is essentially removed from the inflation tube by the syringe, the balloon, of course, collapses. When such a leak or removal of the valve occurs, the catheter must be removed from the patient and a new catheter reinserted. Such a result, of course, causes unnecessary discomfort to the patient and additional effort, time and cost because a second catheter is required. The danger of the inadvertent loosening or removal of the valve by the syringe is especially great where the inflation tube is made of soft or highly elastic plastic such as latex and polyurethane.

A valved catheter as disclosed, for example, in U.S. Pat. No. 3,087,492, has a valve which is frictionally held in place in the proximal end of an inflation tube (7). When fluid is to be inserted into the inflation tube, a syringe tip (T) is inserted into sealing engagement with internal walls of the valve and fluid is pumped from the syringe through the inflation lumen and into the balloon. Depending upon how well the syringe tip is loosened prior to pulling the syringe out of the valve, there could be some forces depending upon the technique used, tending to remove the valve from the inflation tube.

It is a principal object of the present invention to provide a valved medical tube or catheter wherein the above-mentioned disadvantage and problems are substantially obviated.

Another object of the present invention is to provide a catheter such as a Foley catheter having an inflatable balloon and improved means for retaining an inflation valve in an inflation tube connected in fluid communication with the balloon.

Another object is to provide an improved valve retainer for retaining an inflation valve disposed in an end portion of an inflation lumen of a medical tube which prevents inadvertent loosening or withdrawal of the valve from the inflation lumen.

It is another object of the present invention to provide improved means for attaching resilient flexible members or tubes such as are used in medical devices to members insertable therein.

Another object is to provide a relatively inexpensive means for maintaining a member positioned in the end portion of a flexible tubular member.

Another object is to make it difficult if not impossible to remove a member from a position installed in the end portion of a flexible resilient tubular member.

Another object is to simplify the connnection between tubular members and other members.

Another object is to improve the construction of devices that have tubular connections including devices such as relatively delicate medical devices and the like.

In accordance with one aspect of the present invention, a medical tube is provided which has a flexible tube, a valve disposed within an end portion of the tube, and a retainer having tabs extending from one end of the retainer that are deflectable inwardly of the retainer to positions extending adjacent the inner surface of the retainer and the outer portion of the tube so that the tabs prevent withdrawal of the valve from the flexible tube.

These and other objects and advantages of the present invention will become apparent to those skilled in the art after considering the following detailed specification in conjunction with the accompanying drawings.

DETAILED DESCRIPTION OF THE PREFERRED EMBODIMENTS

Figure 1:
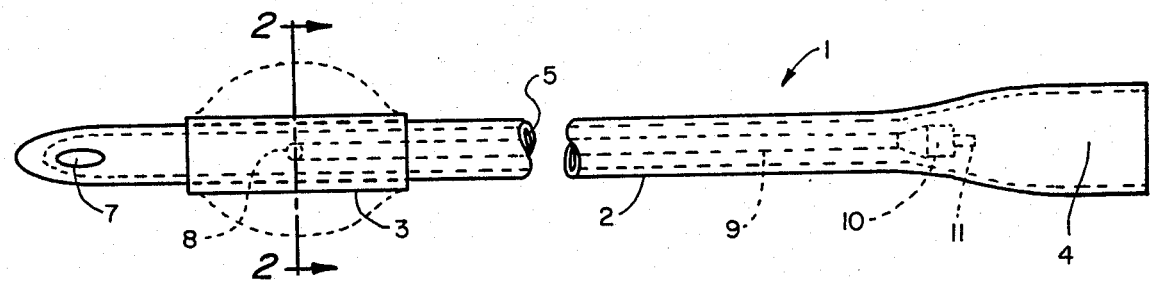
FIG. 1 is a side elevational view of a Foley catheter constructed having incorporated therein a valve retainer means in accordance with one embodiment of the present invention.
Figure 2:
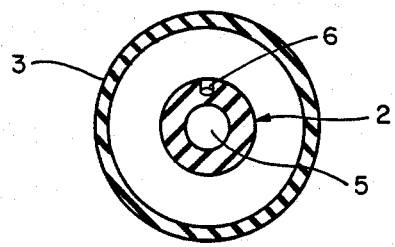
FIG. 2 is a cross-sectional view taken along line 2—2 of FIG. 1.

Referring to the drawings more particularly by reference numbers, number 1 in FIG. 1 refers to one embodiment of a medical device shown as a urinal or Foley catheter adapted to insertion through the urethral canal and into the bladder of a patient for draining urine from the patient. The catheter 1 includes a main catheter tube or shaft 2 having a cuff or balloon 3 surrounding a distal end portion of tube 2 and a radially outwardly tapered connector portion 4 at the proximal end for connection to a drainage tube and urine collection container or bag (not shown). As seen also in FIG. 2, wherein the balloon 3 is inflated, catheter 1 has longitudinally extending main and auxiliary or inflation lumens indicated at 5 and 6, repsectively. Tube 2 has a plurality of openings 7 at the distal end which connect with main lumen 5. An opening 8 which extends into the sidewall of the tube connects the distal end of the inflation lumen with the interior of balloon 3. The proximal end of the inflation lumen is connected with an inflation tube 9 having an inflation valve retainer 10 securing an inflation valve 11 within the proximal end of the inflation tube.

Figure 3:
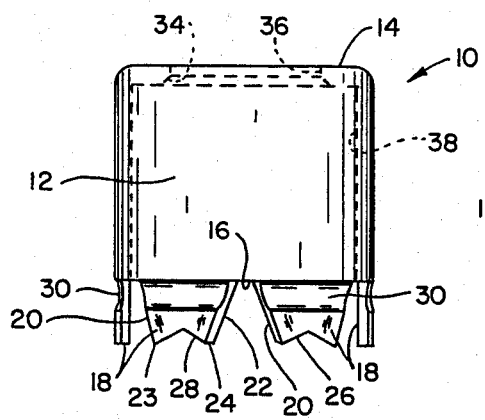
FIG. 3 is a side elevational view of a retainer member constructed according to the teachings of the present invention.
Figure 4:
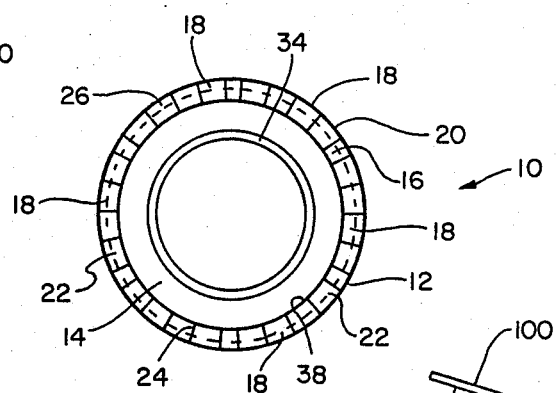
FIG. 4 is a bottom view of the retainer member of FIG. 3.
Figure 5:
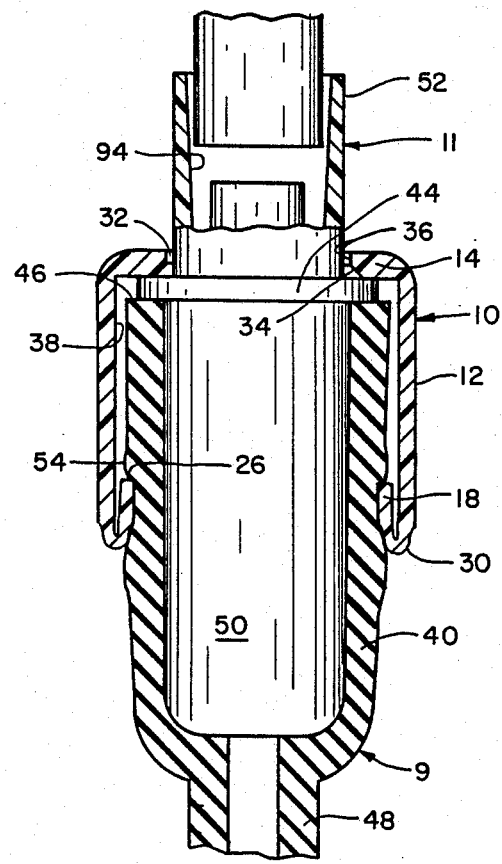
FIG. 5 is an enlarged cross-sectional view through the center of a medical device mounted in the end of a tubular member having the subject retainer means mounted thereon.

The retainer 10, as best seen in FIGS. 3-5, has a tubular wall portion 12 that extends between spaced opposite ends one of which is partially closed by annular flange 14, and the opposite end 16 has a plurality of spaced endwardly extending bendable tabs 18 integrally attached thereto. Each of the tabs 18 has spaced and opposed side walls 20 and 22 which are shown at an angle relative to the axis of the tubular body such that the tabs 18 become narrower from their attached ends to their free ends. The free ends of the tabs are also shown formed with spaced points 23 and 24 formed by the respective side edges 20 and 22 and end edges 26 and 28 as shown. Each of the tabs 18 also has a groove 30 formed in the outer surface thereof making the tabs 18 relatively easy to bend relative to the body portion 12. The entire retainer 10 is preferably constructed of a stiff by relatively resilient plastic material such as a polyolefin, plasticized polyester, nylon or the like. FIG. 4 is a bottom plan view of the retainer 10 shown in FIG. 3 showing the construction with six spaced tabs 18. Also shown in FIG. 4 is the opening 32 formed by the flange 14. The opening may have different shapes including the shape shown in FIGS. 3 and 4 defined by a beveled portion 34 and a cylindrical portion 36 to receive and accommodate the member that extends therethrough. The spacing and tapering of the tabs 18 enables the tabs to be bent to positions adjacent to the inner surface 38 of the retainer without overlapping.

FIG. 5 shows a valve member 11 mounted on tube 9 which is formed of relatively soft and resilient plastic material such as rubber, latex, silicone, polyurethane or other soft polymer. The tube 9 has a tubular proximal end portion 40 shaped to receive the valve 11 which is inserted therein into the position shown. The device 11 has an annular outwardly extending flange portion 44 which bears against the end surface 46 of the tubular end portion 40 and in the embodiment shown, the end portion 40 also is connected to a smaller diameter tubular portion 48 of the tube 9 which is connected at the opposite end to the distal end of inflation lumen 6. The valve 11 has a main cylindrical valve portion 50 which is positioned so as to extend into the tubular member 40, and a smaller diameter endwardly extending or operator portion 52 which extends outwardly from the proximal end of end portion 40 as shown.

When the valve assembly 11 is positioned as described, the subject retainer device 10 can be installed as will be explained. First, it is necessary to the installation to deflect or bend all of the tabs 18 inwardly in order to start moving the retainer 10 onto the tubular end portion 40. With the tabs bent inwardly it is then possible to relatively easily slide the retainer member 10 into its fully seated position as shown. In this position the tabs 18 bear against the outer surface of the end portion 40 deflecting a portion of it inwardly and forming a bulge 54 against the tip portions 23 and 24 and the associated end surfaces 26 and 28. This bulging provides a positive gripping action between the tabs 18 and the end portion 40 making it virtually impossible to remove the retainer member 10 from the inflation tube 9 without destroying or damaging the end portion 40 in the process. It is significant to note that the grooves 30 formed on the outer surfaces of the tabs 18 stretch to the condition shown in FIG. 5 and in so doing narrow the distal end portion of the retainer 10. However, since the tabs are bent inwardly and backwardly, it is relatively easy to start the retainer 10 on the tubular end portion 40 and to complete the sliding thereof onto the outer surface of the portion 40.

Figure 6:
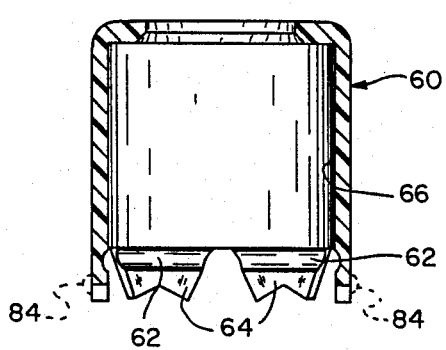
FIG. 6 is a cross-sectional view taken through the center of another embodiment of the subject retainer.
Figure 7:
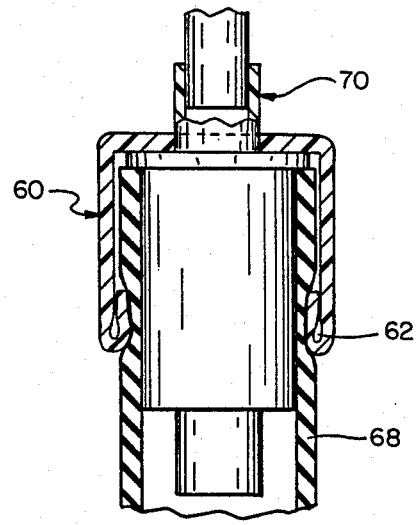
FIG. 7 is a cross-sectional view through the center of a tubular member and a retainer member of the type shown in FIG. 6.

Referring now to FIG. 6, there is shown a modified embodiment 60 of the retainer member which is similar to the retainer 10 except for the fact that grooves 62 in the tabs 64 are formed on the inner rather than the outer surfaces of the tabs. This means that when the tabs are folded inwardly adjacent to the inner surface 66 of the retainer 60 that the folding will produce cavities along the fold lines of the tabs on the inner surfaces thereof. This is shown in FIG. 7 wherein the retainer 60 is shown mounted on the end of a tubular member 68 which may be a flexible tube to hold a valve assembly 70 in place therein. The operation of the retainer device 60 is the same as the retainer device 10 with the difference noted above.

In all forms of the subject retainer the tabs 18 can have optional sidewardly extending projections such as the projections 84 shown in dotted outline in FIG. 6. The projections 84, if used, are located on the sides of the tabs that engage the end portion of the tubes 9 or 68 on which they are installed to provide even greater gripping action.

Figure 8:
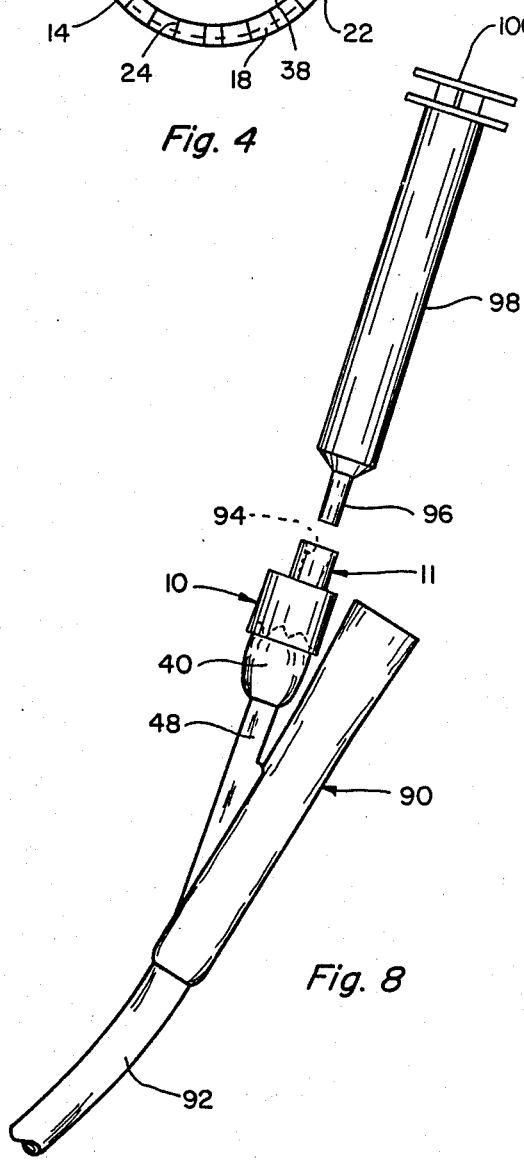
FIG. 8 is a side elevational view of a catheter device having valve means mounted in the end portion of a tubular member and held in place by retainer means constructed according to the present invention.

FIG. 8 shows the proximal end portion of a typical device 90, such as a medical tube or catheter, on which the subject retainers 10 or 60 are installed. The device is a catheter, such as an endotracheal catheter having a main tube 92 which, in use, will extend into the throat. The catheter 90 also has the tubular connection provided by the tube portion 48 which has an enlarged or bulbous end portion similar to the portion 40 described above into which the valve assembly 11 is positioned. The valve assembly 11 has a tubular inlet passageway 94 which cooperates with an outlet tube or tip 96 on a syringe or like device 98. The syringe has a slidable piston 100, which is withdrawn to fill the syringe with a fluid such as air or a liquid such as a saline solution or other medication. The syringe tip 96 is positioned to sealably engage the mating tubular valve inlet tube 94. When so positioned, the piston 100 is moved so as to expel the fluid contained in the syringe through the valve 11 for entry into the catheter tube. For use with catheters incorporating an inflatable member, i.e. a balloon, the syringe can be used to charge air thereto for inflation. The valve will then act to maintain such balloon in inflated condition.

It is apparent that the present retainer means has many different applications other than those described and is especially useful for installing members in the ends of relatively soft flexible plastic or plastic-like substances. It is also important that the valve means installed in tubes in such devices be installed so as to not come apart, work loose, or be damaged. Reliability is extremely important for such devices. It is obvious however that there are many other possible uses and applications for the subject device.

Thus there has been shown and described a novel retainer means which fullfils all of the objects and advantages sought therefor. It will be apparent to those skilled in the art, however, that many changes, modifications, variations and other uses and applications of the subject retainer devices are possible and contemplated. All such changes, modifications, variations and other uses and applications which do not depart from the spirit and scope of the invention are deemed to be covered by the invention which is limited only by the claims which follow.

What is claimed is:

1. Means for attaching the free end of a relatively resilient flexible inflation tube member of a medical device having an inflatable cuff and an inflation valve insertable therein comprising a retainer member having a tubular body sized to have an inner surface to receive an end portion of the inflation tube member when the inflation valve is positioned therein, said retainer member having open opposite proximal and distal ends, an annular flange partially closing the proximal end to abut the inflation valve when the end of the tube member with the inflation valve therein is positioned extending into the retainer member, and a plurality of endwardly extending tabs formed integrally with the distal end of the retainer member, said tabs being deflectable inwardly on the retainer member to positions extending adjacent to the inner surface of the retainer member whereby the end portion of the tube member with the inflation valve therein can relatively easily be moved into the retainer member from the distal end thereof when the tabs are deflected inwardly to adjacent the inner surface thereof, said tabs having end edges which engage the outer surface of the tube member so as to prevent withdrawal of the tube member from the retainer member.

2. The means of claim 1 wherein the retainer member is formed of relatively stiff but resilient plastic.

3. The means of claim 1 wherein the tabs are connected to the distal end of the tubular retainer member by relatively narrow connection portions which facilitate angular deflection of the tabs.

4. The means of claim 3 wherein the connection portions for the tabs are defined by grooves in the outer surfaces of said tabs.

5. The means of claim 3 wherein the connection portion for the tabs are defined by grooves in the inner surfaces of said tabs.

6. The means of claim 1 wherein the resilient tube member is formed of a relatively soft elastomer.

7. The means of claim 1 wherein the tabs have free end edges opposite where they connect to the distal end of the tubular retainer body, said free end edges of each of the tabs having projections that engage the resilient tube member.

8. The means of claim 1 wherein each of the tabs has spaced side and end edges, one of the side edges of each tab being connected to the distal end of the tubular retainer member, the spaced end edges of the tabs being angularly related to each other whereby the tabs are narrower along their free side edges opposite from where they are attached so that adjacent ones of the tabs will not overlap one another when deflected to their positions adjacent to the inner surface of the tubular body.

9. The means of claim 1 wherein the adjacent tabs on the tubular body are spaced from each other.

10. A retainer for installing on the end portion of a flexible tubular member having a device extending therein from one end portion thereof, said retainer comprising a tubular body having an inside surface of cross-sectional size and shape to receive the end portion of the tubular member, said tubular body having one end partially closed by an inwardly extending flange for abutting one end of the device to limit penetration of the tubular member into the retainer, and a plurality of longitudinally extending tabs attached to the end of the retainer member opposite from the annular flange, said tabs being bendable relative to the body from their longitudinally extending positions to positions adjacent to the inside surface of the body whereby when the tabs are adjacent said inside surface the retainer member can be moved onto the end portion of the tubular member.

11. The retainer of claim 10 wherein said annular flange on the opposite end of the tubular body from the tabs limits movement of the body onto the tubular member.

12. The retainer of claim 10 formed of a relatively stiff but flexible plastic.

13. The retainer of claim 10 wherein the device extending into the tubular member from one end thereof includes a valve device.

14. The retainer of claim 10 wherein the tubular member is formed of a relatively soft flexible material.

15. The retainer of claim 14 wherein the tubular member is part of a medical device.

16. A medical tube device comprising a main tube, an inflatable cuff on said main tube, and an inflation tube of relatively compressible material connected in fluid communication with the cuff, an inflation valve disposed in a proximal end portion of said inflation tube, and a retainer for securing said valve in place in said inflation tube end portion, said retainer including a tubular portion with spaced distal and proximal ends and having an inner surface surrounding said tube end portion and said valve, an annular flange partially closing the proximal end thereof to limit movement of the tube with the valve therein into the retainer and a plurality of relatively resilient circumferentially spaced tabs integrally connected to said retainer portion at the distal end thereof, said tabs being deflectable on the retainer inwardly to positions adjacent the inner surface of said retainer portion and the outer surface of said tube end portion positioned therein, said tabs being in frictional engagement with the outer surface of said tube end portion.

17. The catheter of claim 16 wherein the axial length of each of said tabs is greater than the radial distance between the inner surface of said retainer and the outer surface of said proximal end portion of said inflation tube.

18. A Foley catheter comprising a main tube, an inflatable cuff connected adjacent the distal end thereof, cuff inflation means including an inflation tube connected in fluid communication with said cuff, an inflation valve having a portion positioned extending into the inflation tube from the proximal end thereof, and a valve retainer including a tubular portion having a proximal end partially closed by an inwardly extending flange to limit penetration of the inflation tube with the valve therein into the retainer, and a plurality of tabs integrally connected to the distal end of said body portion, said tabs being deflectable to positions extending adjacent to the inner surface of said body portion whereby said proximal end portion of said inflation tube can relatively easily be moved into the retainer member when said tabs are deflected to said positions, said tabs engaging and permitting relatively easy movement of the outer surface of said proximal end portion of said inflation tube in one direction only into the retainer.

19. A medical tube device comprising a main tube including a main lumen, a cuff surrounding a distal end portion of said tube, and inflation lumen means connected at the distal end thereof with the interior of said cuff and at the proximal end thereof to an inflation tube, a check valve disposed in the proximal end portion of said inflation tube, and a retainer for securing said valve in place in said inflation tube including a generally cylindrical portion surrounding said proximal end portion and said valve, an inwardly extending flange partially closing one end of said cylindrical portion, and a plurality of resilient circumferentially spaced tabs integrally connected to said cylindrical portion at the distal end thereof and extending proximally between the inner surface of said cylindrical portion and the outer surface of said proximal end portion of said inflation tube and engaged with the outer surface of said proximal end portion to prevent withdrawal of said valve from said inflation tube, said valve being normally closed to prevent fluid flow therethrough in either direction and openable for selectively introducing and discharging fluid into and out of said inflation lumen means and into and out of the cuff for selectively inflating and deflating said cuff.

20. The medical device of claim 19 wherein said tabs resiliently engage the outer surface of said proximal end portion and the axial length of each of said tabs is greater than the radial distance between the inner surface of said cylindrical portion and the outer surface of said proximal end portion.

* * * * *